United States Patent
Emmenegger et al.

(10) Patent No.: US 6,296,613 B1
(45) Date of Patent: Oct. 2, 2001

(54) 3D ULTRASOUND RECORDING DEVICE

(75) Inventors: Niklaus Emmenegger; Olaf Engfer, both of Zurich (CH)

(73) Assignee: Synthes (U.S.A.), Paoli, PA (US)

( * ) Notice: Subject to any disclaimer, the term of this patent is extended or adjusted under 35 U.S.C. 154(b) by 0 days.

(21) Appl. No.: 09/242,565
(22) PCT Filed: Aug. 22, 1997
(86) PCT No.: PCT/CH97/00311
 § 371 Date: Feb. 19, 1999
 § 102(e) Date: Feb. 19, 1999
(87) PCT Pub. No.: WO98/08112
 PCT Pub. Date: Feb. 26, 1998
(51) Int. Cl.[7] ............................... A61B 8/00
(52) U.S. Cl. .................. 600/459; 600/443; 128/916
(58) Field of Search .................. 600/443, 454, 600/460, 447, 655; 128/916

(56) References Cited

U.S. PATENT DOCUMENTS

| | | | |
|---|---|---|---|
| Re. 35,816 | 6/1998 | Schulz | 356/376 |
| 3,821,469 | 6/1974 | Whetstone et al. | 178/18 |
| 3,983,474 | 9/1976 | Kuipers | 324/43 |
| 4,058,114 | 11/1977 | Soldner | 128/2 |
| 4,146,924 | 3/1979 | Birk et al. | 364/513 |
| 4,160,386 * | 7/1979 | Jackson et al. | 73/625 |
| 4,182,312 | 1/1980 | Mushabac | 433/68 |
| 4,204,225 | 5/1980 | Mistretta | 358/111 |
| 4,209,254 | 6/1980 | Reymond et al. | 356/152 |
| 4,262,306 | 4/1981 | Renner | 358/93 |
| 4,341,220 | 7/1982 | Perry | 128/630 |
| 4,358,856 | 11/1982 | Stivender et al. | 378/167 |
| 4,396,945 | 8/1983 | DiMatteo et al. | 358/107 |
| 4,418,422 | 11/1983 | Richter et al. | 378/205 |
| 4,419,012 | 12/1983 | Stephenson et al. | 356/141 |
| 4,437,161 | 3/1984 | Anderson | 364/414 |
| 4,457,311 | 7/1984 | Sorenson et al. | 128/660 |
| 4,465,069 | 8/1984 | Barbier et al. | 128/303 |
| 4,473,074 | 9/1984 | Vassiliadis | 128/303.1 |
| 4,485,815 | 12/1984 | Amplatz et al. | 128/329 |
| 4,543,959 | 10/1985 | Seponen | 128/653 |
| 4,571,834 | 2/1986 | Fraser et al. | 33/1 |
| 4,583,538 | 4/1986 | Onik et al. | 128/303 |
| 4,592,352 | 6/1986 | Patil | 128/303 |
| 4,598,368 | 7/1986 | Umemura | 364/414 |
| 4,602,622 | 7/1986 | Bär et al. | 128/303 |
| 4,613,866 | 9/1986 | Blood | 343/448 |

(List continued on next page.)

FOREIGN PATENT DOCUMENTS

| | | |
|---|---|---|
| 0 062 941 A1 | 10/1982 | (EP) . |
| 0 326 768 A2 | 8/1989 | (EP) . |
| 0 647 428 A2 | 4/1995 | (EP) . |
| 2 094 590 | 9/1982 | (GB) . |
| WO 90/05494 | 5/1990 | (WO) . |
| WO 91/07726 | 5/1991 | (WO) . |
| WO 94/24933 | 11/1994 | (WO) . |
| WO 95/31148 | 11/1995 | (WO) . |
| WO 96/11624 | 4/1996 | (WO) . |
| WO 97/29685 | 8/1997 | (WO) . |
| WO 97/29709 | 8/1997 | (WO) . |

*Primary Examiner*—Marvin M. Lateef
*Assistant Examiner*—Maulin Patel
(74) *Attorney, Agent, or Firm*—Pennie & Edmonds LLP

(57) ABSTRACT

This invention concerns a device for recording three-dimensional ultrasound images. The device includes an ultrasound head which can be freely moved by hand, an ultrasound recording apparatus, an image processing system, and a position detection system. The position detection system has an analyzing unit and at least two sensors for detecting electromagnetic waves so that the position and orientation of the ultrasound head and, thus, the position and orientation of the ultrasound section images in space can be determined.

21 Claims, 4 Drawing Sheets

U.S. PATENT DOCUMENTS

| | | | |
|---|---|---|---|
| 4,613,942 | 9/1986 | Chen | 364/513 |
| 4,618,978 | 10/1986 | Cosman | 378/164 |
| 4,638,798 | 1/1987 | Shelden et al. | 128/303 |
| 4,649,504 | 3/1987 | Krouglicof et al. | 364/559 |
| 4,651,732 | 3/1987 | Frederick | 128/303 |
| 4,670,781 | 6/1987 | Aubert et al. | 358/93 |
| 4,672,564 | 6/1987 | Egli et al. | 364/559 |
| 4,674,057 | 6/1987 | Caughman et al. | 364/513 |
| 4,729,098 | 3/1988 | Cline et al. | 364/414 |
| 4,733,661 | 3/1988 | Palestrant | 128/303 |
| 4,733,969 | 3/1988 | Case et al. | 356/375 |
| 4,737,032 | 4/1988 | Addleman et al. | 356/376 |
| 4,742,815 | 5/1988 | Ninan et al. | 128/4 |
| 4,743,770 | 5/1988 | Lee | 250/560 |
| 4,743,771 | 5/1988 | Sacks et al. | 250/560 |
| 4,745,290 | 5/1988 | Frankel et al. | 250/360 |
| 4,750,487 | 6/1988 | Zanetti | 128/303 |
| 4,753,528 | 6/1988 | Hines et al. | 356/1 |
| 4,760,851 | 8/1988 | Fraser et al. | 128/774 |
| 4,761,072 | 8/1988 | Pryor | 356/1 |
| 4,762,016 | 8/1988 | Stoughton et al. | 74/479 |
| 4,763,652 | 8/1988 | Brisson et al. | 128/328 |
| 4,764,016 | 8/1988 | Johansson | 356/371 |
| 4,776,749 | 10/1988 | Wanzenberg et al. | 414/680 |
| 4,779,212 | 10/1988 | Levy | 364/562 |
| 4,782,239 | 11/1988 | Hirose et al. | 250/561 |
| 4,791,934 | 12/1988 | Brunnett | 128/653 |
| 4,793,355 | 12/1988 | Crum et al. | 128/653 |
| 4,794,262 | 12/1988 | Sato et al. | 250/560 |
| 4,803,976 | 2/1989 | Frigg et al. | 128/92 |
| 4,821,200 | 4/1989 | Öberg | 364/474.24 |
| 4,821,206 | 4/1989 | Arora | 364/513 |
| 4,822,163 | 4/1989 | Schmidt | 356/1 |
| 4,825,091 | 4/1989 | Breyer et al. | 250/560 |
| 4,829,373 | 5/1989 | Leberl et al. | 358/88 |
| 4,835,710 | 5/1989 | Schnelle et al. | 364/513 |
| 4,836,778 | 6/1989 | Baumrind et al. | 433/69 |
| 4,841,967 | 6/1989 | Chang et al. | 128/303 |
| 4,869,247 | 9/1989 | Howard, III et al. | 128/303.1 |
| 4,875,478 | 10/1989 | Chen | 128/303 |
| 4,896,673 | 1/1990 | Rose et al. | 128/660.03 |
| 4,907,252 | 3/1990 | Aichinger et al. | 378/99 |
| 4,943,296 | 7/1990 | Funakubo et al. | 606/166 |
| 4,945,914 | 8/1990 | Allen | 128/653 |
| 4,955,891 | 9/1990 | Carol | 606/130 |
| 4,970,666 | 11/1990 | Welsh et al. | 364/522 |
| 4,987,488 | 1/1991 | Berci | 358/93 |
| 4,991,579 | 2/1991 | Allen | 128/653 |
| 5,016,639 | 5/1991 | Allen | 128/653 |
| 5,027,818 | 7/1991 | Bova et al. | 128/653 |
| 5,047,036 | 9/1991 | Koutrouvelis | 606/130 |
| 5,050,608 | 9/1991 | Watanabe et al. | 128/653 |
| 5,059,789 | 10/1991 | Salcudean | 250/206.1 |
| 5,078,140 | 1/1992 | Kwoh | 128/653.1 |
| 5,080,662 | 1/1992 | Paul | 606/130 |
| 5,086,401 | 2/1992 | Glassman et al. | 395/94 |
| 5,094,241 | 3/1992 | Allen | 128/653.1 |
| 5,097,839 | 3/1992 | Allen | 128/653.1 |
| 5,099,846 | 3/1992 | Hardy | 128/653.1 |
| 5,107,839 | 4/1992 | Houdek et al. | 128/653.1 |
| 5,119,817 | 6/1992 | Allen | 128/653.1 |
| 5,142,930 | 9/1992 | Allen et al. | 74/469 |
| 5,178,164 | 1/1993 | Allen | 128/898 |
| 5,186,174 | 2/1993 | Schlöndorff et al. | 128/653.1 |
| 5,197,476 | 3/1993 | Nowacki et al. | 128/660.03 |
| 5,198,877 | 3/1993 | Schulz | 356/375 |
| 5,207,223 | 5/1993 | Adler | 128/653.1 |
| 5,211,164 | 5/1993 | Allen | 128/653.1 |
| 5,211,165 | 5/1993 | Domoulin et al. | 128/653.1 |
| 5,230,338 | 7/1993 | Allen et al. | 128/653 |
| 5,230,623 | 7/1993 | Guthrie et al. | 433/72 |
| 5,249,581 | 10/1993 | Horbal et al. | 128/664 |
| 5,251,127 | 10/1993 | Raab | 364/413.13 |
| 5,257,998 | 11/1993 | Ota et al. | 606/130 |
| 5,274,551 | 12/1993 | Corby, Jr. | 364/413.13 |
| 5,278,756 | 1/1994 | Lemchen et al. | 364/413.28 |
| 5,295,483 | 3/1994 | Nowacki et al. | 128/660.03 |
| 5,299,288 | 3/1994 | Glassman et al. | 395/80 |
| 5,300,080 | 4/1994 | Clayman et al. | 606/130 |
| 5,305,203 | 4/1994 | Raab | 364/413.13 |
| 5,309,913 | 5/1994 | Kormos et al. | 128/653.1 |
| 5,320,462 * | 6/1994 | Johansson et al. | 409/84 |
| 5,325,855 | 7/1994 | Daghighian et al. | 128/653.1 |
| 5,350,351 | 9/1994 | Saffer | 601/2 |
| 5,383,454 | 1/1995 | Bucholz | 128/653.1 |
| 5,389,101 | 2/1995 | Heilbrun et al. | 606/130 |
| 5,408,409 | 4/1995 | Glassman et al. | 364/413.13 |
| 5,445,166 | 8/1995 | Taylor | 128/897 |
| 5,479,597 | 12/1995 | Fellous | 395/154 |
| 5,483,961 | 1/1996 | Kelly et al. | 128/653.1 |
| 5,494,034 | 2/1996 | Schlöndorff et al. | 128/653.1 |
| 5,588,430 | 12/1996 | Bova et al. | 128/653.1 |
| 5,603,318 * | 2/1997 | Heilbrun et al. | 600/426 |
| 5,617,857 | 4/1997 | Chader et al. | 128/653.1 |
| 5,622,170 | 4/1997 | Schulz | 128/653.1 |
| 5,630,431 | 5/1997 | Taylor | 128/897 |
| 5,631,973 | 5/1997 | Green | 382/128 |
| 5,662,111 | 9/1997 | Cosman | 128/653.1 |
| 5,676,673 | 10/1997 | Ferre et al. | 606/130 |
| 5,682,886 | 11/1997 | Delp et al. | 128/653.1 |
| 5,690,113 * | 11/1997 | Sliwa, Jr. et al. | 600/443 |
| 5,711,299 | 1/1998 | Manwaring et al. | 128/653.1 |
| 5,729,129 | 3/1998 | Acker | 324/207.12 |
| 5,732,703 | 3/1998 | Kalfas et al. | 128/653.2 |
| 5,735,278 | 4/1998 | Hoult et al. | 128/653.2 |
| 5,748,767 | 5/1998 | Raab | 382/128 |
| 5,755,725 | 5/1998 | Druais | 606/130 |
| 5,769,078 | 6/1998 | Kliegis | 128/653.1 |
| 5,772,593 | 6/1998 | Hakamata | 600/407 |
| 5,795,294 | 8/1998 | Luber et al. | 600/407 |
| 5,800,352 | 9/1998 | Ferre et al. | 600/407 |
| 5,810,008 | 9/1998 | Dekel et al. | 128/660.07 |
| 5,829,444 | 11/1998 | Ferre et al. | 128/897 |
| 5,848,967 | 12/1998 | Cosman | 600/426 |
| 5,851,183 * | 12/1998 | Bucholz | 600/407 |
| 5,891,034 * | 4/1999 | Bucholz | 600/427 |
| 5,911,691 * | 6/1999 | Mochizuki et al. | 600/443 |
| 5,921,992 * | 7/1999 | Costoles et al. | 606/130 |
| 6,186,948 * | 2/2001 | Kamiyama et al. | 600/443 |
| 6,186,949 * | 2/2001 | Hatfiled et al | 600/443 |
| B1 5,383,454 | 12/1996 | Bucholz | 128/653.1 |

* cited by examiner

3D ULTRASOUND RECORDING DEVICE

FIELD OF THE INVENTION

This invention relates to an ultrasound imaging system, a three-dimensional ultrasonographic-image acquisition device as specified in the independent patent claim and a procedure for the acquisition of three-dimensional ultrasound images.

BACKGROUND OF THE INVENTION

A system for determining the position of a sensor within a given object and for the display of previously recorded images of the object corresponding to the sensor position has been described earlier by BUCHHOLZ in U.S. Pat. No. 5,383,454. With that system it is also possible to guide the tip of a sensor to a particular location within an object, while the position of the sensor can be observed on a monitor screen which also displays a previously recorded image of that particular region within the object. In that earlier concept, the position of the sensor is determined using a commercially available, three-dimensional sound digitizer.

Another example of an earlier method and appropriate system for the acquisition of diagnostically useful, three-dimensional ultrasound image data has been described by POLZ in the European patent EP 0 736 284 A2. That system incorporates a device by means of which it is possible, by freely and manually guiding the ultrasound scanning head, to assemble from a set of three-dimensional data tomographic images of an entire three-dimensional volume object or space to be examined. The position and orientation of the ultrasound scanning head are registered by an additional, electromagnetic sensor system. The ultrasound scanning head, freely guided by hand by the diagnostician, is preferably provided with a holder which also accommodates the receiver of the said electromagnetic sensor system. The sensor system whose receiver coils pick up magnetic fields emitted by a transmitter, produces sensor output data (both positional and rotational data) which precisely define the spatial position and orientation of the ultrasound scanning head. These are translational X, Y and Z axis data as well as rotational data around these axes.

A prerequisite for sufficiently precise positional and orientational determinations using magnetic field measurements is very detailed information on such extraneous parameters as:

- interference fields generated for instance by display monitors, computers or electric motors;
- interference patterns produced by highly permeable materials in the magnetic field, for instance metal objects moving within the measuring region; or
- electromagnetic interference fields emanating from the AC power supply.

SUMMARY OF THE INVENTION

Quantifying these effects and/or minimizing them by appropriate hardware or procedures, be it shielding or continuous calibration, is a complex matter. The drawback of the earlier concept referred to thus lies in the fact that it is difficult to obtain positional and orientational determinations with the necessary degree of accuracy.

It is the objective of this invention to solve the problem. Its purpose is to provide a means for acquiring three-dimensional ultrasonographic images using a freely movable, manually guided ultrasound scanning head, an ultrasound acquisition device and a positional-determination i.e. locating device, which locating device permits the determination of the position and orientation of the ultrasound scanning head and thus of the spatial position and orientation of the tomographic ultrasound images.

The advantages offered by this invention consist essentially in the fact that the conceptual design of the device here disclosed simplifies the manipulation conditions in the following manner:

- in terms of precise resolution, the system is not affected by external parameters;
- the system is easy to handle; even if the positional determination were to be disrupted for instance by an object that strayed in between the acquisition device and the ultrasound scanning head, measurements can continue as soon as a clear view is restored; and
- the tracking accuracy is not negatively affected by extraneous electromagnetic fields produced by display monitors and/or electrical equipment.

The present invention relates to an ultrasound imaging system for creating a three-dimensional image of a patient body. The system includes an ultrasound scanning head for acquiring a plurality of ultrasound images, a fixed control plane for determining position and orientation of the ultrasound scanning head relative to a spatial base by linear measurement, transmitters for emitting electromagnetic waves associated with either base points on the spatial base or control points on the control plane, receivers for receiving the electromagnetic waves located on the other of the base points or the control points, and an image processor for processing the ultrasound images to create the three-dimensional image of the body. The electromagnetic waves are used to determine the position and orientation of the ultrasound scanning head to thereby position and orient the plurality of ultrasound images.

In another aspect of the present invention, the ultrasound imaging system includes a freely movable, manually guided ultrasound scanning head for acquiring a plurality of ultrasound images, an ultrasound acquisition device for storing and displaying the plurality of ultrasound images, an image processor for processing the plurality of ultrasound images to create the three-dimensional image of the body, and a positional locating device for determining position and orientation of the ultrasound scanning head to thereby position and orient the plurality of ultrasound images. The locating device has a plurality of electromagnetic wave emitting devices located on the ultrasound scanning head, a plurality of electromagnetic wave sensor arrays for detecting the electromagnetic waves of the emitting devices, and an evaluation unit for computing the position and orientation of the ultrasound scanning head relative to a spatial base by linear measurements based on the electromagnetic waves.

The present invention relates to an ultrasound imaging system for creating a three-dimensional image of a patient body. The system includes an ultrasound scanning head for acquiring a plurality of ultrasound images, a fixed control plane for determining position and orientation of the ultrasound scanning head relative to a spatial base by linear measurement, transmitters for emitting electromagnetic waves associated with either base points on the spatial base or control points on the control plane, receivers for receiving the electromagnetic waves located on the other of the base points or the control points, and an image processor for processing the ultrasound images to create the three-dimensional image of the body. The eletromagnetic waves are used to determine the position and orientation of the ultrasound scanning head to thereby position and orient the plurality of ultrasound images.

In another aspect of the present invention, the ultrasound imaging system includes a freely movable, manually guided ultrasound scanning head for acquiring a plurality of ultrasound images, an ultrasound acquisition device for storing displaying the plurality of ultrasound images, an image processor for processing the plurality of ultrasound images to create the three-dimensional image of the body, and a positional locating device for determining position and orientation of the ultrasound scanning head to thereby position and orient the plurality of ultrasound images. The locating device has a plurality of electromagnetic wave emitting devices located on the ultrasound scanning head, a plurality of electromagnetic wave sensor arrays for detecting the electromagnetic waves of the emitting devices, and an evaluation unit for computing the position and orientation of the ultrasound scanning head relative to a spatial base by linear measurements based on the eletromagnetic waves.

In one implementation of the concept of this invention, the means provided on the ultrasound scanning head to emit electromagnetic waves for positional and orientational determinations are in the form of optical light sources.

In another implementation of the concept of this invention, the means provided on the ultrasound scanning head to emit electromagnetic waves for positional and orientational determinations are in the form of infrared light emitting diodes (IRLEDs).

In a different implementation of the concept of this invention, the means provided on the ultrasound scanning head to emit electromagnetic waves for positional and orientational determinations are in the form of reflectors or electrofluorescent reflectors.

In another implementation of the concept of this invention, the means provided on the ultrasound scanning head to emit electromagnetic waves for positional and orientational determinations are in the form of fiber optics connected to a light source.

In yet another implementation of the concept of this invention, the sensor systems serving to detect the electromagnetic waves within the measuring region are in the form of spatially fixed, unidimensional (linear-array) cameras, allowing an evaluation unit to determine the position and orientation of the ultrasound scanning head and thus the spatial position and orientation of the tomographic ultrasound images.

In another implementation of the concept of this invention, the sensor systems serving to detect the electromagnetic waves within the measuring region are cameras which are not spatially fixed, the position of the cameras being detectable by the acquisition and evaluation of a spatially fixed control-point reference field which in turn allows the evaluation unit to determine the spatial position and orientation of the tomographic ultrasound images. The acquisition and evaluation of the spatially fixed control-point reference field thus permits real-time measurements even under unstable environmental conditions. Every time the cameras acquire an image, the control-point reference field is used to recalculate the current camera positions, fully compensating for any positional changes of the cameras.

In another implementation of the concept of this invention, the sensor systems serving to detect the electromagnetic waves within the measuring region are spatially fixed, permitting the positional and orientational determination of a spatially variable control-point reference field for instance on a patient.

In yet another implementation of the concept of this invention, at least two of the sensors serving to detect the electromagnetic waves within the measuring region are spatially fixed cameras, allowing an evaluation unit to videogrammetrically determine the position and orientation of the ultrasound scanning head and thus the spatial position and orientation of the tomographic ultrasound images.

In a different implementation of the concept of this invention, the said minimum of two sensors serving to detect the electromagnetic waves within the measuring region are cameras which are not spatially fixed, the position of the cameras being determined by the acquisition and evaluation of a spatially fixed control-point reference field, allowing the evaluation unit to videogrammetrically determine the position and orientation of the ultrasound scanning head and thus the spatial position and orientation of the tomographic ultrasound images. The acquisition and evaluation of the spatially fixed control-point reference field thus permits real-time measurements even under unstable environmental conditions. Every time the cameras acquire an image, the control-point reference field is used to recalculate the current camera positions, fully compensating for any positional changes of the cameras.

In yet another implementation of the concept of this invention, the freely movable, manually guided ultrasound scanning head, the ultrasound acquisition device, the image processing unit and the positional locating device are connected to a computer-assisted surgery system (CAS).

One application of the procedure according to this invention is based on the design implementation in which the means provided on the ultrasound scanning head to emit electromagnetic waves for positional and orientational determinations are in the form of optical light sources.

Another application of the procedure according to this invention is based on the design implementation in which the means provided on the ultrasound scanning head to emit electromagnetic waves for positional and orientational determinations are in the form of infrared light emitting diodes (IRLEDs).

Another application of the procedure according to this invention is based on the design implementation in which the means provided on the ultrasound scanning head to emit electromagnetic waves for positional and orientational determinations are in the form of reflectors or electrofluorescent reflectors.

Another application of the procedure according to this invention is based on the design implementation in which the devices provided on the ultrasound scanning head to emit electromagnetic waves for positional and orientational determinations are in the form of fiber optics connected to a light source.

Yet another application of the procedure according to this invention is based on the design implementation in which the sensor systems serving to detect the electromagnetic waves within the measuring region are in the form of spatially fixed, unidimensional cameras, allowing an evaluation unit to determine the position and orientation of the ultrasound scanning head and thus the spatial position and orientation of the tomographic ultrasound images.

Another application of the procedure according to this invention is based on the design implementation in which the sensor systems serving to detect the electromagnetic waves within the measuring region are cameras which are not spatially fixed, the position of the cameras being detectable by the acquisition and evaluation of a spatially fixed control-point reference field which in turn allows the evaluation unit to determine the spatial position and orientation of the tomographic ultrasound images. The acquisition and evaluation of the spatially fixed control-point reference field thus permit real-time measurements even under unstable environmental conditions. Every time the cameras acquire an image, the control-point reference field is used to recalculate the current camera positions, fully compensating for any positional changes of the cameras.

Another application of the procedure according to this invention is based on the design implementation in which the sensor systems serving to detect the electromagnetic waves within the measuring region are spatially fixed, permitting the positional and orientational determination of a spatially variable control-point reference field for instance on a patient.

Yet another application of the procedure according to this invention is based on the design implementation in which at least two sensors serving to detect the electromagnetic waves within the measuring region are spatially fixed cameras, allowing an evaluation unit to videogrammetrically determine the position and orientation of the ultrasound scanning head and thus the spatial position and orientation of the tomographic ultrasound images.

Another application of the procedure according to this invention is based on the design implementation in which the said minimum of two sensors serving, to detect the electromagnetic waves within the measuring region are cameras which are not spatially fixed, the position of the cameras being determined by the acquisition and evaluation of a spatially fixed control-point reference field, allowing the evaluation unit to videogrammetrically determine the position and orientation of the ultrasound scanning, head and thus the spatial position and orientation of the tomographic ultrasound images. The acquisition and evaluation of the spatially fixed control-point reference field thus permits real-time measurements even under unstable environmental conditions. Every time the cameras acquire an image, the control-point reference field is used to recalculate the current camera positions, fully compensating for any positional changes of the cameras.

A different application of the procedure according, to this invention is based on the design implementation in which the freely movable, manually guided ultrasound scanning, head, the ultrasound acquisition device, the image processing unit and the positional locating device are connected to a computer-assisted surgery system (CAS).

The principles of optical and photogrammetric positional determination employed in this invention are described, inter alia, in the following textbook:

Jordan/Eggert/Kneissl

Handbuch der Vermessungskunde (manual of geodetic surveying)

10th edition, completely revised

Vol. IIIa/3

Photogrammetry

J. B. Metzlersche Verlagsbuchhandlung, Stuttgart, 1972

(see in particular paragraphs 144, 145, 146, 147).

As used herein, the terms 'interference measurements' and 'linear measurements' refer not only to the kind of interference measurements employed for instance in laser ranging but also, and especially, to the interference effects by virtue of which optical systems can produce images (for instance central perspectives) along an image plane or line.

Moreover, the term linear measurements is intended to express longitudinal measurements along an image plane (or line) (for instance on a CCD chip), such as the linear measurement of the distance $z_1$, $z_2$, in FIG. 4 (par. 146.2, FIG. 5 in the geodetic surveying manual), as well as absolute measurements of the length of the object of interest, as employed for instance in run-length measuring methodology (for example in a GPS system).

In lieu of the method shown in FIG. 4, employing two projection planes, it is also possible to use a measuring method which is likewise based on the array principle but employs at least 3 non-colinear, unidimensional CCD chips. One such product is commercially available, by the name of Optotrak™.

BRIEF DESCRIPTION OF THE DRAWINGS

The following will describe this invention and its conceptual enhancements in more detail, with the aid of partly schematic illustrations of several design examples in which.

DETAILED DESCRIPTION OF THE PREFERRED EMBODIMENTS

Figure 1:
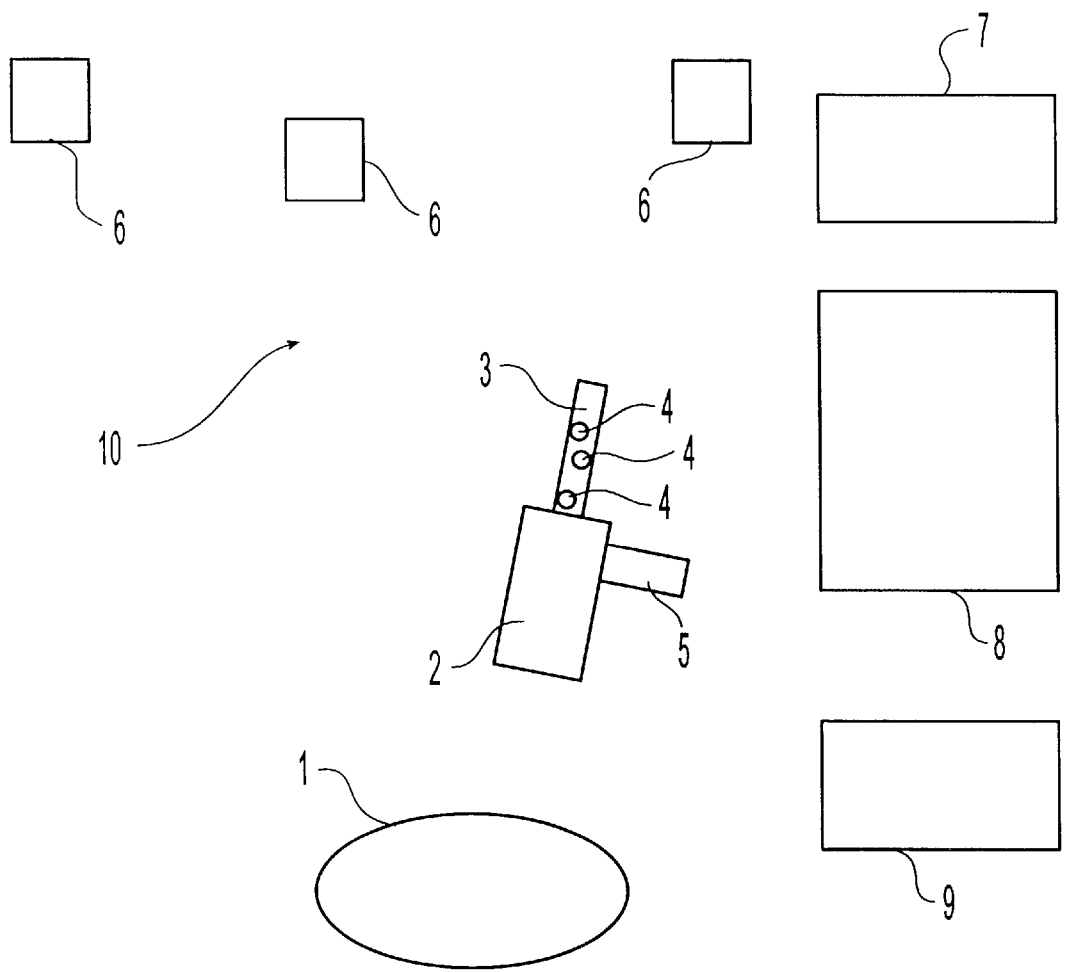
FIG. 1 is a schematic representation of one design version of the system according to this invention.

The design version of the system according to this invention as shown in FIG. 1 includes a freely movable, manually operated ultrasound scanning head 2, an ultrasound recording i.e. acquisition device 9, an image processing unit 8 and a positional locating device 10, serving to acquire three-dimensional ultrasound images of the body 1. The locating device 10 permits positional and orientational determination of the ultrasound scanning head 2 and thus the determination of the spatial position and orientation of the tomographic ultrasound images. Mounted on the ultrasound head 2 are transmitters 4 which emit electromagnetic waves. Spatially fixed cameras 6, for example digital cameras, are provided and serve to capture the said electromagnetic waves emitted by the transmitters 4. The transmitters 4 are imaged on the ultrasound scanning head 2. The evaluation unit 7 then computes from these images the position and orientation of the ultrasound scanning head 2. With the aid of a handle 5, the operator can freely move the ultrasound scanning head 2 and is thus able to assemble a complete three-dimensional tomographic image of the body 1 as derived from the three-dimensional data record defined in the image processing unit.

Figure 2:
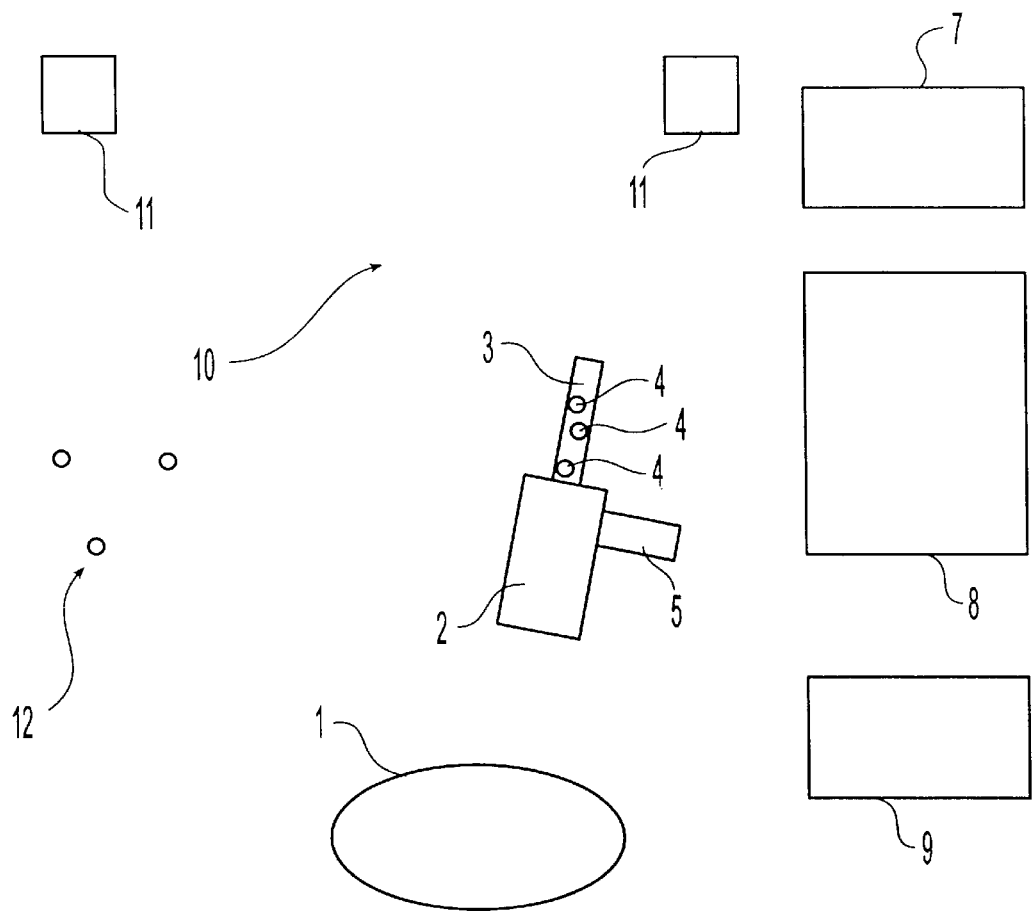
FIG. 2 is a schematic representation of another design version of the system according to this invention.

FIG. 2 shows a design version of the system according to this invention, which includes a freely movable, manually guided ultrasound scanning head 2, an ultrasound acquisition device 9, an image processing unit 8, a positional locating device 10 and a control-point reference field 12 consisting of light-emitting diodes (LEDs), serving to acquire three-dimensional ultrasonographic images of the body 1. The locating device 10 permits positional and orientational determination of the ultrasound scanning head 2 and thus the determination of the spatial position and orientation of the tomographic ultrasound images. Attached to the ultrasound scanning head 2 are transmitters 4 which emit electromagnetic waves. Cameras 6, for example digital cameras, serve to capture the said electromagnetic waves emitted by the transmitters 4. In this implementation of the invention, the cameras 6 are not spatially fixed, their position 11 being determined by the acquisition and evaluation of the images produced by a spatially fixed control-point reference field 12. As the two cameras 6 capture the electromagnetic waves emitted by the transmitters 4, these transmitters 4 are imaged on individual image planes. The evaluation unit 7 then computes from the distorted perspectives of the two images the position and orientation of the ultrasound scanning head 2. With the aid of a handle 5, the operator can freely move the ultrasound scanning head 2 and is thus able to assemble a complete three-dimensional tomographic image of the body 1 as derived from the three-dimensional data record defined in the image processing unit.

Figure 3:
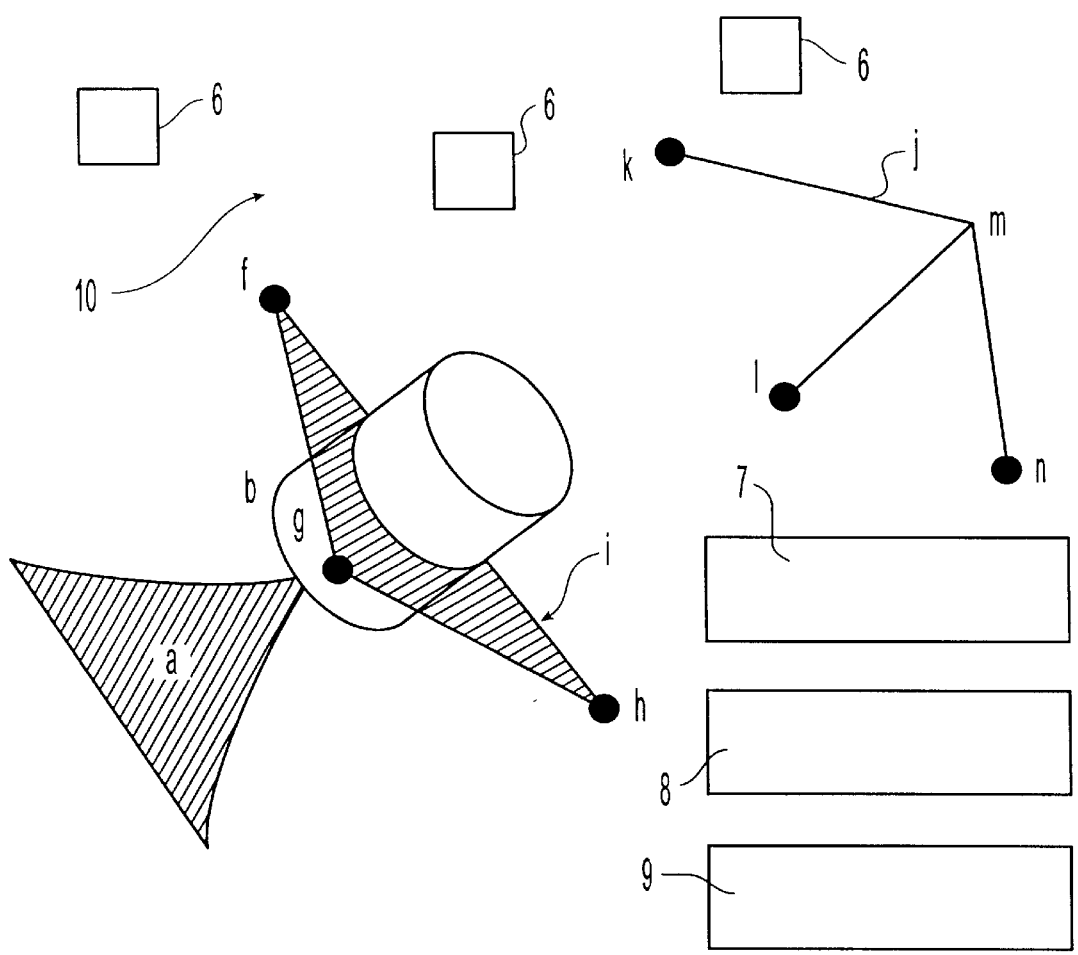
FIG. 3 is a schematic representation of yet another design version of the system according to this invention.

FIG. 3 shows a design version of the system according to this invention, which includes a freely movable, manually guided ultrasound scanning head b, an ultrasound acquisition device 9, an image processing unit 8 and a positional locating device 10 for the acquisition of ultrasound images a. The positional locating device 10 permits positional and orientational determination of the ultrasound scanning head b and thus the determination of the spatial position and orientation of the tomographic ultrasound images a. Connected to the ultrasound scanning head b are fixed transmitters f;g;h which emit electromagnetic waves. Spatially fixed cameras 6, for instance digital cameras, are provided for recording the electromagnetic waves emitted by the transmitters f;g;h. The cameras 6 capture these electromagnetic waves emitted by the transmitters f;g;h and from the images thus acquired the evaluation unit 7 then calculates the position and orientation of the ultrasound scanning head b. With the aid of a handle 5, the operator can freely move the ultrasound scanning head b and is thus able to assemble a complete three-dimensional tomographic image of the body as derived from the three-dimensional data record defined in the image processing unit.

Figure 4:
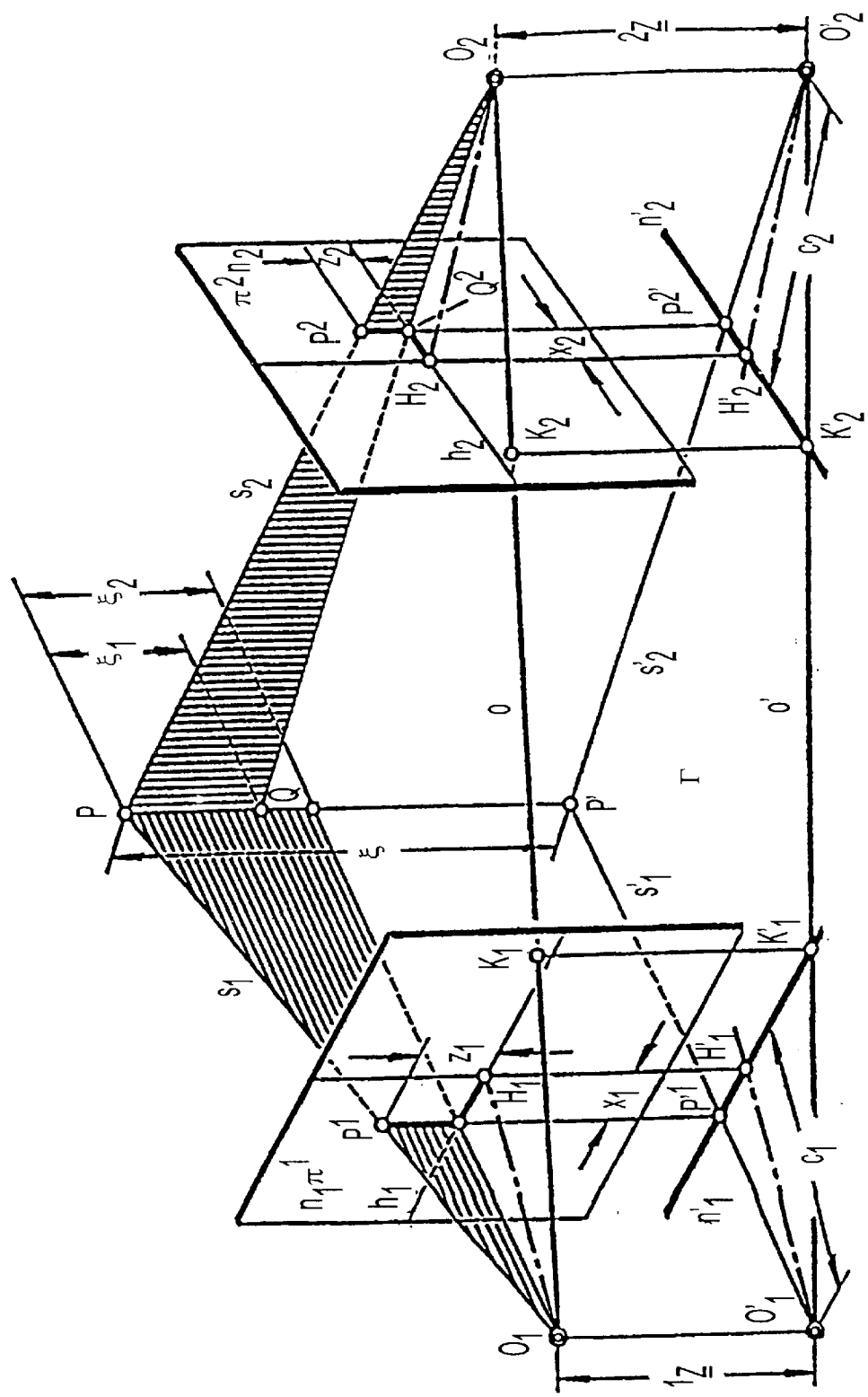
FIG. 4 is a schematic illustration serving to explain the photogrammetric procedure.

FIG. 4 is intended to explain the photogrammetric method employed using the specific example titled "reconstruction (of the coordinates) from two perspective views with known positions of the image planes relative to each other and with known internal orientation", as per Jordan/Eggert/Kneissl, manual of geodetic surveying, 1972, page 2271:

146.2 Reconstruction from two perspective views with known positions of the image planes relative to each other and with known internal orientation:

Given the respective internal orientation, one knows the visual rays $[O_1], [O_2]$ and their position relative to the image planes. Knowing the mutual position of the image planes thus means knowing the mutual position of the visual ray bundles. The known spatial position of $\Pi_1, \Pi_2, O_1, O_2$ yields the core axis o, the straight line $s=(\Pi_1 \Pi_2)$, the epipoles $K_1$, $K_2$ and the perspective allocation of the epipolar ray bundles relative to s. For any image pair $P^1$, $P^2$ tied to corresponding epipolar rays, this will ensure that the visual rays $s_1=[O_1 P^1]$ and $s_2=[O_2 P^2]$ will intersect at a spatial point P. One thus knows the position of P in the system of visual ray bundles. To determine the position of P in a given spatial reference system S one must know the position of $_{1, 2}$ within S. If the latter is not readily available, it must be determined per par. 145.3. As an example of an empirical, nonautomatic reconstruction, the following will address the so-called plane-table photogrammetry.

a) In plane-table photogrammetry (FIG. 4) <(a), in its simplest representation, with CCD chips to be assigned to the image planes $_{1, 2}$>

$\Gamma$ is assumed to be a horizontal plane (planimetric plane). The image planes $\Pi_1, \Pi_2$ are assumed to be vertical, i.e. the main visual rays $[O_1, H_1], [O_2, H_2]$ to be horizontal. $h_1, h_2$ constitute the image horizontal in $\Pi_1, \Pi_2$. $x_1, z_1$ and $x_2, z_2$, respectively, are the image coordinates in $_1$ and $_2$, respectively. The point of origin of each image coordinate system is the main point, the x-axis points extend in the horizontal direction. $\check{z}_1, \check{z}_2$ are assumed to represent the height of the central points $O_1, O_2$ above $\Gamma$.

It is also possible from the coordinates $x_1, x_2$ of any given image points $P^1$, $P^2$ to enter into the known planimetric planes $\Pi'_1, \Pi'_2$ the planimetric planes $P^{1'}$, $P^{2'}$, identifying the planimetric plane P' of the spatial point P to be reconstructed as a cross section of the planimetric visual-ray planes $s'_1=[O'_1 P'_1]$ and $s'_1=[O'_2 P'_2]$ (forward section. While the base line $O'_1 O'_2$ is applied at the map scale, the image widths and x-coordinates will be multiplied by a suitable factor in a manner which will allow $s'_1, s'_2$ to be traced with sufficient accuracy.

From the similar triangles $O_2 PQ$ and $O_2 P^2 Q^2$ one can derive the height $\zeta_2$ of P above the plane $[O_2 h_2]$ via $$\zeta_2 = \frac{z_2 O'_2 P'}{O'_2 P'_2}$$

This yields the height $\zeta$ of P above $\Gamma$ by way of $\zeta=\check{z}_2+\zeta_2$. By means of an analogous calculation of $\zeta=\check{z}_1+\zeta_1$ one can compensate for any errors.

As is shown in FIG. 4, the planimetric planes $K'_1, K'_2$ of the epipoles $K_1, K_2$ are determined as intersections i.e. crossover points of the baseline $o'=[O'_1 O'_2]$ with $\Pi'_1, \Pi'_2$, their respective height above $\Gamma$, meaning their position in $\Pi_1, \Pi_2$, is found by inverting the trapezoid $O'_1 O'_2 O_2 O_1$, dragging along the vertical carrier line for $K_1$ and $K_2$. The epipolar rays are needed for identifying appropriate epipoles in the images of object characteristics.

If the image planes $\Pi^{1*}, \Pi^{2*}$ were to be in some general spatial position, one could easily revert to the case, just discussed, of vertical image planes $\Pi_1, \Pi_2$. One would only have to reproject $\pi^{1*}$ from $O_1$ to $\Pi_1$ and $\pi^{2*}$ from $O_2$ to $\Pi_2$. Without such reprojection, the total of the points P' per FIG. 4 would make up the normal plane of the imaged object on a plane perpendicular to $\Pi^{1*}$ and $\Pi^{2*}$ and $\zeta$ would be the distance between point P and this plane.

What is claimed is:

1. An ultrasound imaging system for creating a three-dimensional ultrasound image of a patient body comprising:

an ultrasound scanning head for acquiring a plurality of ultrasound images, each of the plurality of ultrasound images having a uniquely defined position relative to a spatial base defined by plural base points;

a fixed control plane for determining position and orientation of the ultrasound scanning head relative to the spatial base by linear measurement, the fixed control plane freely selectable relative to the ultrasound scanning head and defined by plural control points;

transmitters for emitting electromagnetic waves associated with one of the plural base points or the plural control points;

receivers for receiving the electromagnetic waves located on the other of the plural base points or the plural control points; and an image processor for relating the plurality of ultrasound images to one another to create the three-dimensional ultrasound image of the body, wherein the electromagnetic waves are used to determine the position and orientation of the ultrasound scanning head to thereby position and orient the plurality of ultrasound images.

2. The ultrasound imaging system of claim 1 wherein the linear measurement for determining the position and orientation of the ultrasound scanning head uses interference effects or run-length measurement.

3. The ultrasound imaging system of claim 1 wherein the receivers are located on the control points and the transmitters are located on the base points.

4. The ultrasound imaging system of claim 1 wherein each transmitter emits electromagnetic waves of a different frequency.

5. The ultrasound imaging system of claim 1 wherein the ultrasound scanning head is a freely movable, manually guided ultrasound scanning head.

6. The ultrasound imaging system of claim 1 further comprising an evaluation unit for computing the position and orientation of the ultrasound scanning head.

7. The ultrasound imaging system of claim 6 further comprising at least two intra-spatially operating electromagnetic wave detecting sensors for determining the position and orientation of the ultrasound scanning head and thereby each of the plurality of ultrasound images.

8. The ultrasound imaging system of claim 7 wherein the sensors are spatially fixed uni-dimensional cameras.

9. The ultrasound imaging system of claim 8 wherein the evaluation unit videogrammetrically determines the position and orientation of the ultrasound scanning head.

10. The ultrasound imaging system of claim 8 wherein position and orientation of a spatially variable control-point reference field is determined by the cameras.

11. The ultrasound imaging system of claim 10 wherein the reference field is located on the patient.

12. The ultrasound imaging system of claim 7 wherein the sensors are uni-dimensional cameras which are not spatially fixed wherein position of each of the cameras is determined by acquisition and evaluation of images of a spatially fixed control-point reference field.

13. The ultrasound imaging system of claim 12 wherein the evaluation unit videogrammetrically determines the position and orientation of the ultrasound scanning head.

14. The ultrasound imaging system of claim 12 wherein the reference field is located on the patient.

15. The ultrasound imaging system of claim 7 wherein the sensors are digital cameras.

16. The ultrasound imaging system of claim 1 wherein the transmitters are infrared light emitting diodes (IRLED's).

17. The ultrasound imaging system of claim 1 wherein the transmitters are fiber optics connected to a light source.

18. The ultrasound imaging system of claim 1 wherein the transmitters are fluorescence reflectors.

19. The ultrasound imaging system of claim 1 wherein the transmitters are optical light sources.

20. The ultrasound imaging system of claim 1 wherein the system is connected to a computer-assisted surgery system (CAS).

21. An ultrasound imaging system for creating a three-dimensional ultrasound image of a patient body comprising:
   a freely movable, manually guided ultrasound scanning head for acquiring a plurality of ultrasound images;
   an ultrasound acquisition device for storing and displaying the plurality of ultrasound images;
   an image processor for relating the plurality of ultrasound images to one another to create the three-dimensional ultrasound image of the body; and
   a positional locating device for determining position and orientation of the ultrasound scanning head to thereby position and orient the plurality of ultrasound images, the locating device including:
      a plurality of electromagnetic wave emitting devices located on the ultrasound scanning head;
      a plurality of electromagnetic wave sensor arrays for detecting the electromagnetic waves of the emitting devices; and
      an evaluation unit for computing the position and orientation of the ultrasound scanning head relative to a spatial base by linear measurements based on the electromagnetic waves.

* * * * *